United States Patent
Kolberg et al.

(10) Patent No.: US 10,173,054 B2
(45) Date of Patent: Jan. 8, 2019

(54) IMPLANTABLE DEVICE

(71) Applicant: BIOTRONIK SE & CO. KG, Berlin (DE)

(72) Inventors: Gernot Kolberg, Berlin (DE); Jens Rump, Berlin (DE); Michael Friedrich, Kleinmachnow (DE); Heinrich Buessing, Berlin (DE); Stefan Knorr, Berlin (DE); Andreas Bitzer, Zurich (CH); Kerstin Teaubert, Berlin (DE); Ingo Weiss, Berlin (DE); Klaus Bartels, Berlin (DE); Michelle Maxfield, Berlin (DE); Hartmut Lenski, Glienicke (DE); Timo Frenzel, Berlin (DE); Erik Trip, Uffelte (NL)

(73) Assignee: BIOTRONIK SE & CO. KG, Berlin (DE)

( * ) Notice: Subject to any disclaimer, the term of this patent is extended or adjusted under 35 U.S.C. 154(b) by 783 days.

(21) Appl. No.: 14/475,634

(22) Filed: Sep. 3, 2014

(65) Prior Publication Data
US 2015/0080694 A1    Mar. 19, 2015

Related U.S. Application Data (60) Provisional application No. 61/877,298, filed on Sep. 13, 2013.

(51) Int. Cl.
*A61N 1/08*    (2006.01)
*A61B 5/00*    (2006.01)
*A61N 1/05*    (2006.01)

(52) U.S. Cl.
CPC .............. *A61N 1/08* (2013.01); *A61B 5/6846* (2013.01); *A61N 1/05* (2013.01); *A61N 1/056* (2013.01); *A61N 1/086* (2017.08)

(58) Field of Classification Search
CPC . A61N 1/08; A61N 1/056; A61N 1/05; A61N 2001/086; A61B 5/6846;
(Continued)

(56) References Cited

U.S. PATENT DOCUMENTS

2007/0112398 A1*  5/2007  Stevenson ................ A61N 1/05
                                                                607/63
2008/0033497 A1   2/2008  Bulkes et al.
(Continued)

FOREIGN PATENT DOCUMENTS

EP    2486952 A1    8/2012

OTHER PUBLICATIONS

European Search Report dated Aug. 29, 2014, 5 pages.

*Primary Examiner* — Eunhwa Kim
(74) *Attorney, Agent, or Firm* — ARC IP Law, PC; Joseph J. Mayo (57) ABSTRACT

An implantable medical device including at least one elongate electrical line with a first electrical component as a functional conductor, and at least one second electrical component with an electrical length. The first electrical component includes a proximal end and a distal end, wherein the distal side is in electrical contact with tissue or blood. The first electrical component is in electrical contact with the at least one second electrical component, and wherein the electrical length of the at least one second component corresponds to at least a tenth of a wavelength ($\lambda/10$) of electromagnetic waves in a radiofrequency range.

16 Claims, 9 Drawing Sheets

(58) Field of Classification Search
CPC ..... A61B 5/042; A61B 5/0422; A61B 5/6852; A61B 5/6869
See application file for complete search history.

(56) References Cited

U.S. PATENT DOCUMENTS

| | | |
|---|---|---|
| 2008/0243218 A1 | 10/2008 | Bottomley et al. |
| 2010/0211129 A1 | 8/2010 | Goedeke et al. |
| 2011/0087302 A1* | 4/2011 | Ameri .................... A61N 1/056 607/9 |
| 2012/0078333 A1* | 3/2012 | Westlund ................ A61N 1/05 607/118 |
| 2012/0109261 A1 | 5/2012 | Stancer et al. |
| 2013/0204335 A1 | 8/2013 | Lloyd et al. |

* cited by examiner

IMPLANTABLE DEVICE

This application claims the benefit of U.S. Provisional Patent Application 61/877,298 filed on 13 Sep. 2013, the specification of which is hereby incorporated herein by reference.

BACKGROUND OF THE INVENTION

Field of the Invention

Embodiments of the invention generally relate to a permanently or temporarily implantable medical device including an elongate electrical conductor.

Description of the Related Art

Implantable medical devices, for example electrode lines for electrostimulation, have the disadvantage that their electrical conductor heats up in an electromagnetic alternating field, for example in an MRI scanner, because electromagnetic alternating fields induce electrical currents in the electrical conductor.

Specifically, at least one stimulation electrode line is typically connected to implantable cardiac pacemakers or defibrillators. At a proximal end of the line, which is intended for connection to the cardiac pacemaker or defibrillator, there is generally a standardized electrical terminal, and at a distal end of the line, which is intended for placement in the heart, there is generally one or more electrode poles. Typically, an electrode pole is used to deliver electrical pulses, for example to the tissue (myocardium) of the heart or to sense electrical fields in order to sense activity, for example cardiac activity, within the scope of what is known as "sensing".

For this purpose, two electrode poles typically form electrically conductive surface portions of an electrode line. The electrode poles are typically provided as ring electrodes in the form of a ring around the electrode line or in the form of a point electrode or tip electrode at the distal end of the electrode line.

The electrode poles are electrically conductively connected, via one or more electrical conductors, to contacts of the electrical terminal of the electrode line at the proximal end thereof. One or more electrical conductors, which electrically connect one or more of the electrode poles to one or more contacts, thus run between the contacts of the electrical terminal of the electrode lines, at the proximal end thereof, and the electrode poles at the distal end of the electrode line. These electrical conductors are be used for transmission of stimulation pulses to the electrode poles and/or for transmission of electrical signals, received by means of the electrode poles, to the proximal end of the electrode line. The electrical conductors are also referred to herein as functional conductors.

Generally, another disadvantage of typical implantable medical devices include the use of filter elements integrated into the electrode body. The electrode line structure is thus weakened in terms of the electrode line physiological properties, wherein the electrode line is larger and more rigid, such that the risk of tissue irritation and perforation increases. In addition, typically, the filter elements are located in the therapeutic path. As such, generally, the longevity of the structure or construction is thus jeopardized or restricted. Band-stop filters, which are typically used, are frequency selective.

Generally, functional conductors are electrical conductors necessary for the functions of the respective electrode line and, as such, are typically exposed to the risk that electrical currents will be induced in them as a result of external alternating magnetic fields. Typically, this may lead to an undesired heating of the functional conductors or of the electrode poles connected thereto, or may lead to delivery of corresponding currents via the electrode poles to surrounding tissue and therefore heating of the surrounding tissue.

As such, in view of the above, there is a need for a medical device, such as an electrode line, that is impaired as little as possible by electromagnetic alternating fields. In addition, there is a need for an implantable medical device wherein heating of an electrode line or of a catheter in an MRI scanner is reduced.

BRIEF SUMMARY OF THE INVENTION

One or more embodiments of the invention enable a medical device and in particular an electrode line that is impaired as little as possible by electromagnetic alternating fields. For example, the heating of an electrode line or of a catheter in an MRI scanner is reduced.

This is achieved in accordance with one or more embodiments of the invention by a temporarily or permanently implantable medical device including at least one elongate electrical line with a first electrical component and at least one second electrical component. In at least one embodiment, the electrical line or electrode line contains a functional conductor as a first electrical component or part of the first electrical component, wherein the functional conductor may be connected to at least one electrode pole to deliver therapy signals or to detect diagnosis signals. In one or more embodiments, the at least one second electrical component is in electrical contact with the first electrical component, and may for example include an electrical length that corresponds to at least one tenth of a wavelength of electromagnetic waves in a radio frequency range.

At least one embodiment of the invention includes an elongate medical device, wherein the electrical functional conductor or line is thus supplemented by a further electrical line component, such that minimized amplitude of a coupled-in electromagnetic (EM) wave is applied at the location at which an electrical signal is decoupled.

According to one or more embodiments, the implantable medical device, such as the electrode line, that transforms energy for at least one specific wavelength in the electrical line. For example, the energy that is coupled in, via electromagnetic or magnetic alternating fields, at the point at which electrical signals (for example stimulation or sensing signals) are decoupled, and specifically the amplitude of coupled-in electromagnetic waves is minimized. One or more embodiments may include a parallel incorporation or connection of the heat-reducing second electrical component in series for example, such that the effects on the function of the implantable medical device are reduced and damage to the second electrical component does not pose a risk for the functionality of the implantable medical device. At least one embodiment of the invention includes a high level of flexibility of the electrode line, in terms of the geometric design, which enables implementation of the electrode line using established design concepts.

In accordance with at least one embodiment of the invention an implantable body with at least one first elongate electrically conductive component implements at least one first electrical component as a functional conductor having a proximal and a distal end, and at least one second electrical component. In one or more embodiments at least at one point on the distal side, the first electrical component has electrical contact with tissue and/or blood. In at least one embodiment, the first electrical component has electrical contact with the at least one second electrical component. In one or more embodiments, the at least one second electrical component may include an electrical length that corresponds at least to a tenth of a wavelength ($\lambda/10$) of electromagnetic waves in the radio frequency range.

Embodiments of the invention thus provide advantageous physiological properties, implemented with a smaller and more flexible electrode line. The risk of tissue irritation and perforation decreases and the longevity of the construction is increased.

In at least one embodiment, the implantable medical device may include, or may be, an electrode line that connects to a therapy and/or monitoring device, or may be formed as part of a therapy and/or monitoring device. In one or more embodiments, the electrode line may include an inner conductor, such as a functional conductor, wherein the inner conductor may constitute the first electrically conductive component. In at least one embodiment, the implantable medical device may be a passive implant, for example a surgical pin, which in this case also constitutes a functional conductor (albeit an atypical functional conductor) and therefore may constitute the first electrical component.

In one or more embodiments, the electrode line includes a proximal end that may be connected to a therapy and/or monitoring device, and a distal end remote from the proximal end. In at least one embodiment, the electrode line may include at least one electrode pole and the at least one second electrode component arranged at the distal end of the electrode line.

In at least one embodiment, the at least one second electrical component may be wound about a longitudinal portion of the electrode line.

In one or more embodiments, the at least one second electrical component may include an electrical conductor, wherein the electrical conductor may be coiled, in a meandering manner, or may be wound helically or in a spiraled manner, or may be both coiled and wound. As such, in at least one embodiment, the at least one second electrical component may include outer dimensions which are much smaller than the electrical length of the electrical conductor.

In one or more embodiments, the first electrical component has a proximal end and a distal end, wherein the first electrical component and the at least one second electrical component are electrically interconnected at a contact point located in the region of the distal end of the first electrical component. In at least one embodiment, the electrical conductor of the at least one second electrical component may extend in the proximal or distal direction of the first electrical component, starting from the contact point.

In one or more embodiments, the at least one second electrical component may include insulation and may be insulated along its length.

According to at least one embodiment, starting from a contact point of the first electrically conductive component, the at least one second electrical component may be guided in the distal direction or in the proximal direction of the electrode line. One or more embodiments of the invention may include two or more second electrical components, wherein one of the two or more second electrical components may be guided in a proximal direction, and another one of the two or more second electrical components may be guided in a distal direction. In at least one embodiment, the at least one second electrical component may be divided in parallel into two or more conductors.

In at least one embodiment, the at least one second electrical component may be insulated only in some portions along its length. As such, in one or more embodiments, the at least one second electrical component may be guided further in an insulated manner on the other side of a distal contact point and/or on another possible contact point on the proximal side thereof.

In one or more embodiments, the at least one second electrical component may include an electrical length that may correspond to a quarter of the wavelength ($\lambda/4$) of electromagnetic waves in the frequency range from 10 MHz to 400 MHz.

According to at least one embodiment, a distance between the point of the electrical contact between the first electrical component and the one or more second electrical components (this point also referred to herein as the contact point), and at least one distal electrical end of the at least one conductive second electrical component may include an order of magnitude such that the distances may not be reduced macroscopically in the radio frequency range.

By way of at least one embodiment, the distance between tissue contact and at least one line end of the at least one second electrical component, $(2*n+1)*\lambda/4$ ($n \in \mathbb{N}_0$), may be one wavelength $\lambda$ in the radio frequency range. In one or more embodiments, n, a natural number, may be in the range between n=0 and n=2.

In at least one embodiment, the implantable medical device, such as the electrode line, enables tissue contact to occur at a distance*$\lambda/2$ of a wavelength $\lambda$ in the radiofrequency range from the at least one line end of the at least one second electrical component. In one or more embodiments, n is a natural number ($n \in \mathbb{N}$), and may be in the range of n=1 to n=2.

One or more embodiments, as discussed above and as will be discussed below, may be combined with one another, at least in part.

In one or more embodiments, the at least one second electrical component may be divided in parallel into two or more conductors.

In at least one embodiment, the end of the conductor of the at least one second electrical component may be electrically open.

According to one or more embodiments of the invention, the end of the conductor of the at least one second electrical component may be connected electrically capacitively, inductively or galvanically to the tissue. In at least one embodiment, the end of the conductor of the at least one second electrical component may be electrically connected to the point of tissue contact, such as to an electrode pole that contacts the tissue.

In one or more embodiments, the conductor of the at least one second electrical component may connect, at least at one place, to the point of tissue contact (for example to the electrode pole) by one or more capacitively acting elements.

By way of at least one embodiment, the conductor of the at least one second electrical component may connect, at least at one place, to the point of tissue contact (for example to the electrode pole) by one or more inductively acting elements.

In one or more embodiments, the conductor of the at least one second electrical component may connect, at least at one place, to the point of tissue contact (for example to the electrode pole) by a combination of inductively and capacitively acting elements.

In at least one embodiment, the conductor of the at least one second electrical component may connect, at least at one place, to the point of tissue contact (for example to the electrode pole) by one or more electronic switches, diodes, transistors, thyristors or Z-diodes.

According to one or more embodiments, the conductor of the at least one second electrical component may be surrounded completely or in part by a dielectrically effective medium, which may include a relative permittivity ($\varepsilon_R$) greater than 10, greater than 100 or greater than 1000. In at least one embodiment, the dielectrically effective medium, in which the at least one second electrical component may contact, may include, completely or in portions, one or more materials of glass, barium titanate, polyethylene, silicon oxide, silicon carbide, ceramic, piezo materials, aluminum oxide, titanium oxide, tantalum oxide, semiconductor materials, and plastics containing additions of the above-mentioned materials.

In at least one embodiment, the combination of the at least one second electrical component and the dielectric medium may be in contact with an electrically conductive surface. Such a contact, in at least one embodiment, may act as a ground plate and may increase the effective permittivity of the device.

By way of at least one embodiment, the conductor of the at least one second electrical component may be formed from or include any of, or combination of a wire/strip, platinum-plated wire/strip, turned wire/strip, stranded wire, cable, compressed conductor, cut conductor, etched conductor, wire wool/strip wool, galvanically deposited conductor, and a slotted conductive surface.

In one or more embodiments, the conductor materials may be formed from or include any of, or combination of copper, silver, gold, steel, MP35N, carbon, conductive plastics, aluminum, niobium, molybdenum, tantalum, titanium, platinum, and metals.

According to at least one embodiment, the implantable medical device may be used with a limited frequency range and wavelength range, such as a frequency range of an electromagnetic alternating field from 40 MHz to 150 MHz.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
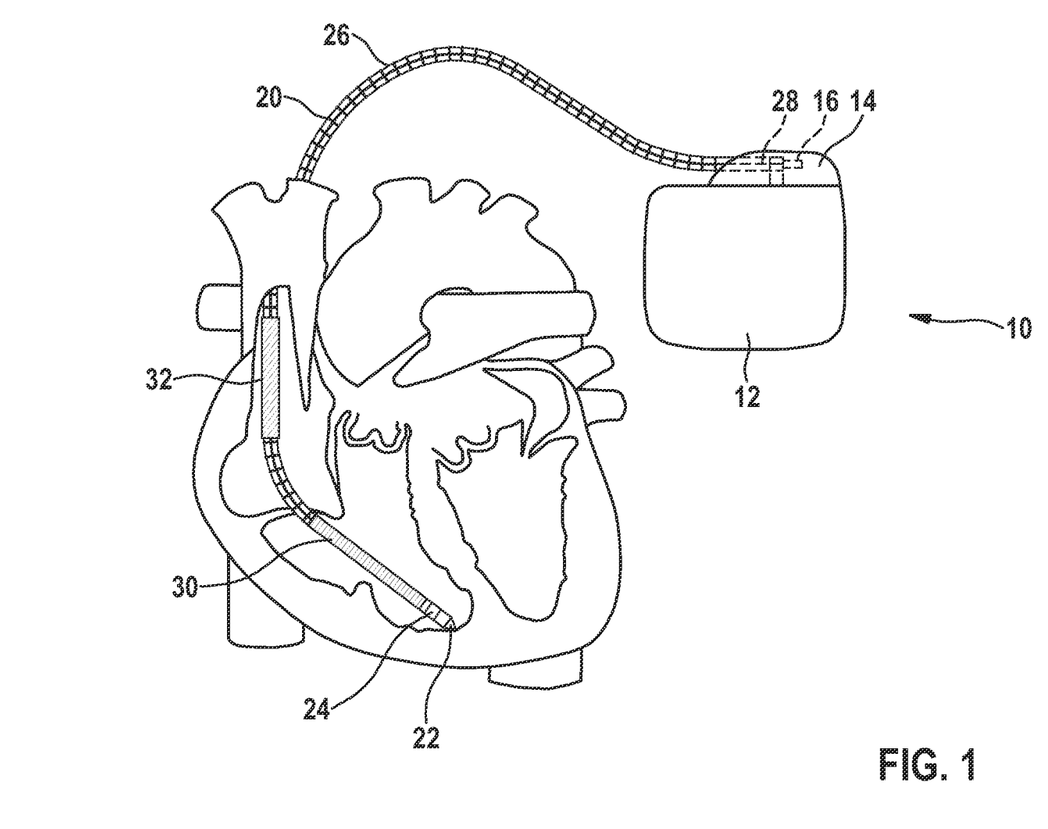
FIG. 1: shows an implantable heart stimulator and an implantable electrode line connected thereto, according to at least one embodiment of the invention.

FIG. 1 shows an implantable heart stimulator 10 and an implantable electrode line 20 connected thereto, according to at least one embodiment of the invention.

In one or more embodiments, the implantable heart stimulator 10 may include a cardiac pacemaker or an implantable cardioverter-defibrillator (ICD). In at least one embodiment of the invention, the heart-stimulator 10 may include a ventricular cardiac pacemaker and defibrillator, a dual-chamber cardiac pacemaker that stimulate a right atrium and a right ventricle of the heart, or a biventricular cardiac pacemaker that stimulates the right ventricle and a left ventricle of the heart. One or more embodiments of the invention may include an all-monitoring device to monitor the heart. At least one embodiment of the invention may include an implantable stimulator with therapy function, monitoring function or both a therapy and a monitoring function device.

In one or more embodiments, the implantable heart stimulator 10 may include a housing 12, which may include metal, may be electrically conductive and may be used as a large-area electrode pole. In at least one embodiment, a terminal housing 14 may be included or fastened on an outer face of the housing 12, and is also referred to as a header. In at least one embodiment, the header may include contact sockets to receive plug contacts. In one or more embodiments, the contact sockets may include electrical contacts 16 that may be connected, via appropriate conductors, to an electronics system located in the housing 12 of the heart stimulator 10.

By way of at least one embodiment, the electrode line 20 may include an implantable medical device. At least one embodiment of the invention may include electrode poles, such as a point or tip electrode 22 and a ring electrode 24, located at a distal end of the electrode line 20. The electrode poles 22 and 24, in one or more embodiments, are utilized, depending on the function of a heart stimulator to which the electrode line 20 is connected, to sense electrical potentials of the heart tissue (myocardium) or to deliver electrical signals, for example to deliver stimulation pulses to the surrounding heart tissue, or both to sense and to deliver. FIG. 1 shows how the electrode poles, such as the tip electrode 22 and the ring electrode 24, in at least one embodiment, may be located in an apex of the right ventricle of the heart.

In one or more embodiments, both the tip electrode 22 and the ring electrode 24 may be electrically connected, via at least one electrical functional conductor 26, to a plug contact 28 at a proximal end of the electrode line 20. In at least one embodiment, the plug contact 28 may include electrical contacts that correspond to the electrical contacts 16 of the contact socket in the terminal housing 14 of the implantable heart stimulator 10.

According to one or more embodiments, the electrical conductors 26 in the electrode line 20 may be formed in, and include, different length portions as approximately elongate cable conductors or as helically coiled conductors. In at least one embodiment, the conductors, which may electrically conductively connect the functional electrode poles to electrical contacts of the plug contact at the proximal end of the electrode line 20, include functional conductors. In one or more embodiments, the functional conductors may transmit electrical signals used for therapy from the plug contact to the respective electrode pole or may guide sensed signals representing electrical potentials from the respective electrode pole to the plug contact, and are therefore used for the basic function of the medical device.

By way of at least one embodiment, the electrical functional conductors 26, which connect the electrode poles 22 and 24 to the electrical contacts of the plug 28 of the electrode line 20, may be surrounded, completely or over a majority of their length, by an insulating sleeve, such that electrical contact with the tissue of the heart, is produced selectively via the electrode poles.

In one or more embodiments, the electrode line 20 may include the electrode poles 22 and 24 used to stimulate the heart tissue (such as ventricular stimulation), and the electrode line 20 may include two electrode poles 30 and 32. In at least one embodiment, the electrode poles 30 and 32 may include a greater area than electrode poles 22 and 24, and may be used as defibrillation electrodes, and may include at least one bare helically coiled wire.

Figure 2:
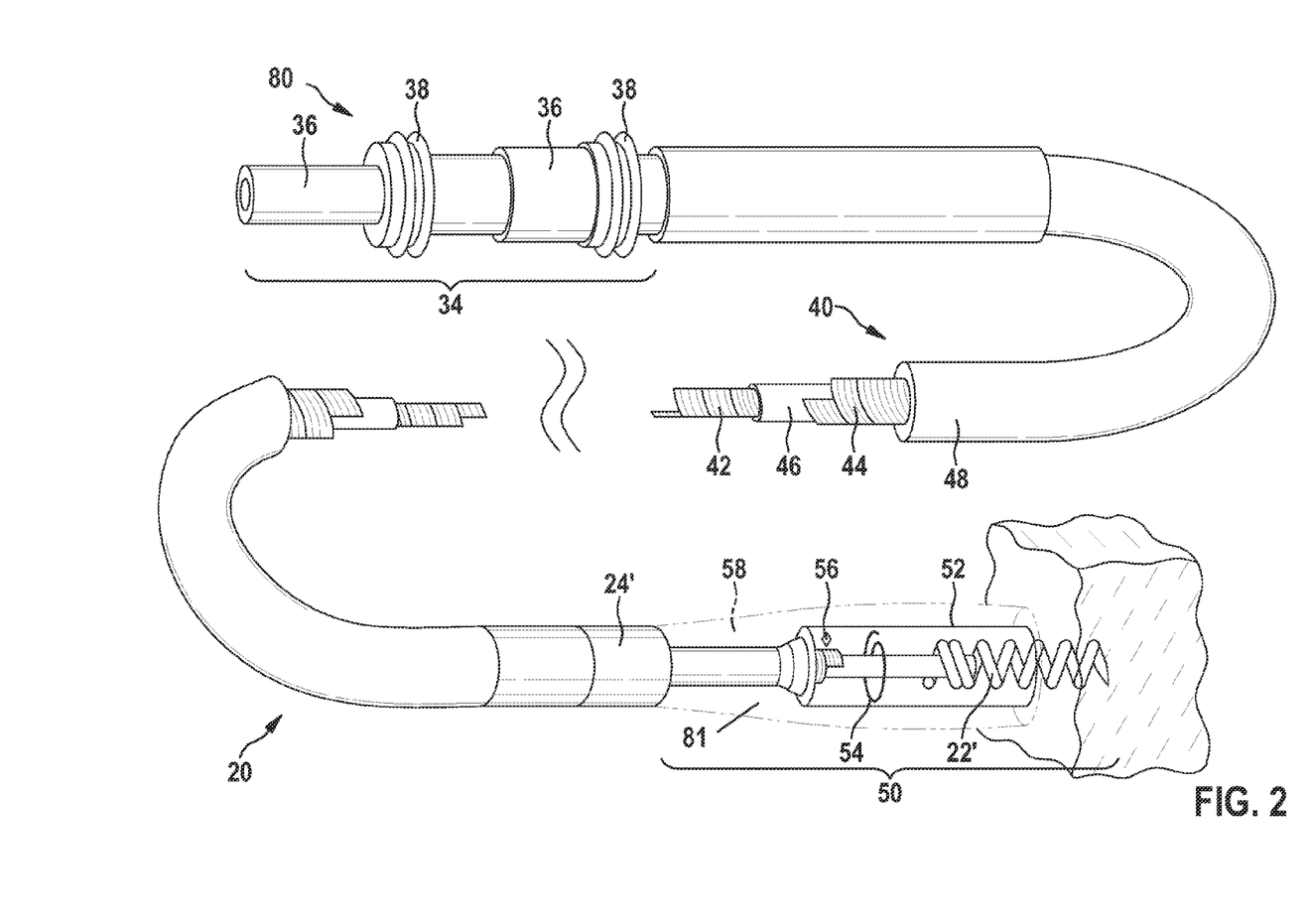
FIG. 2: shows an actively fixable electrode line, according to at least one embodiment of the invention.
Figure 5:
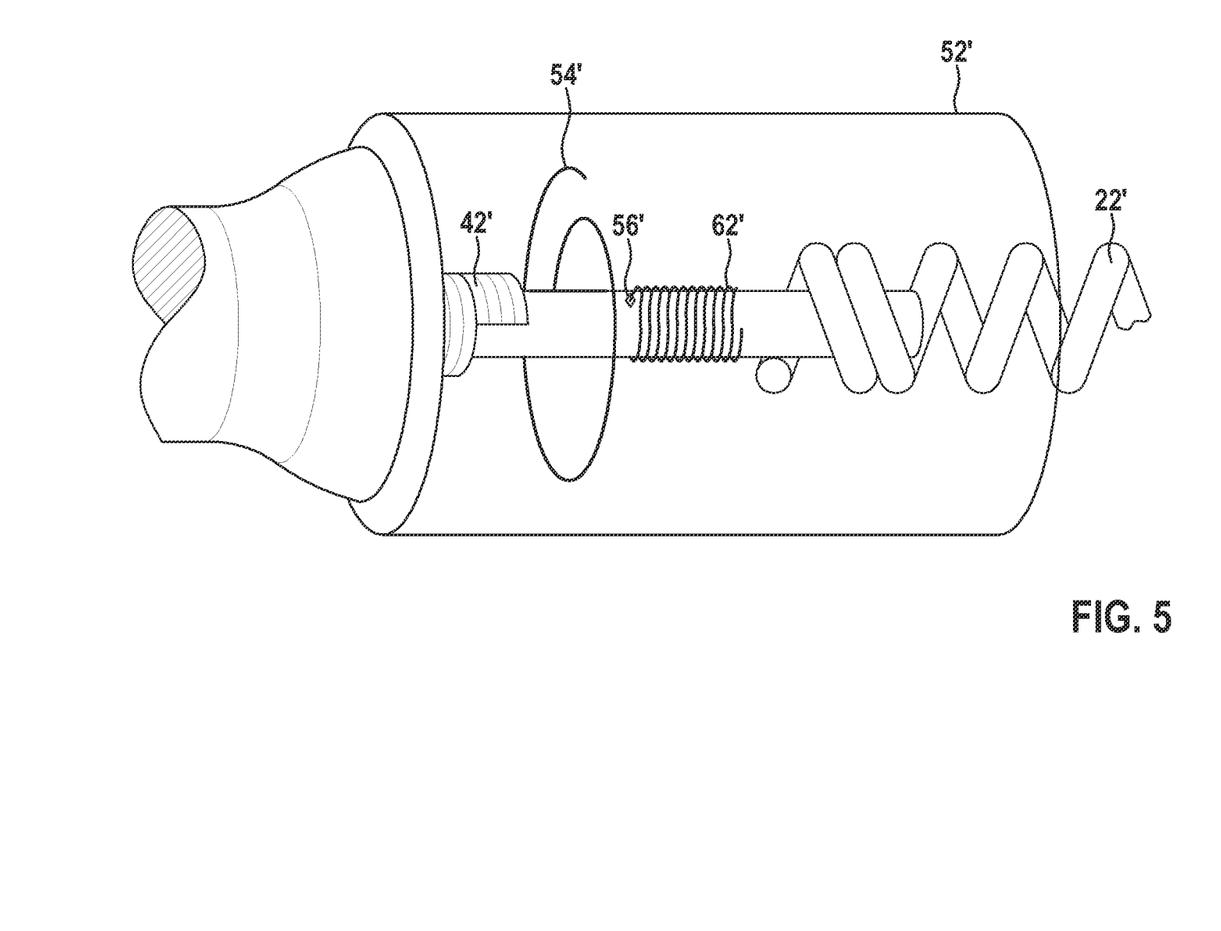
FIG. 5: shows a detail of the distal end of an actively fixable electrode line of FIG. 2 with an electrical conductor wound around a central functional conductor as a second electrical component, according to at least one embodiment of the invention.
Figure 7:
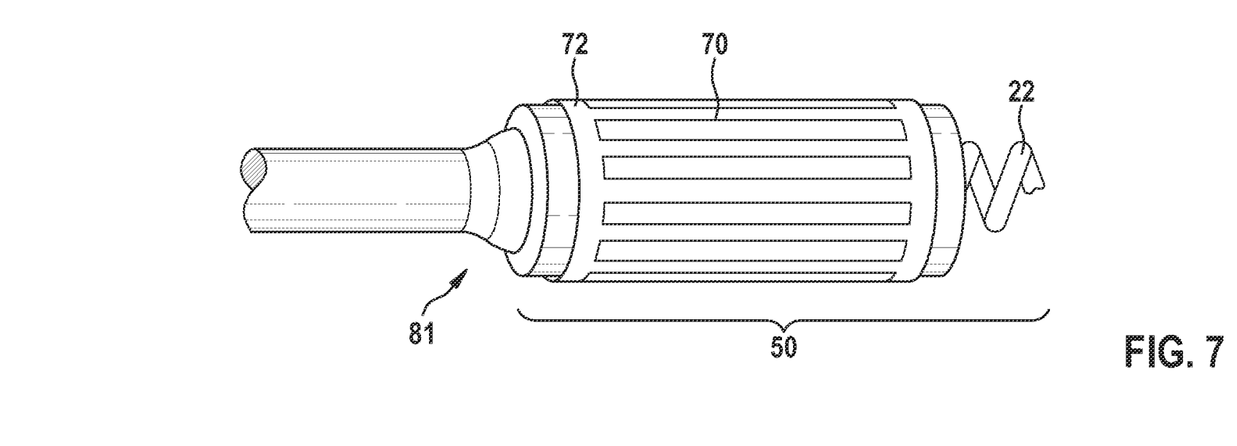

As shown at least in FIGS. 2, 5 and 7, in one or more embodiments, the tip electrode 22 may include an actively fixable electrode pole, such as a corkscrew-like helix. As such, in at least one embodiment, the electrode line 20 may include an actively fixable electrode line.

One or more embodiments of the invention include a right-ventricular cardiac pacemaker and defibrillator, and may include an ablation electrode line as the implantable medical device or as part of the implantable medical device. In at least one embodiment, the ablation electrode line may protrude into a patient's heart and may be controlled by and connected to a device located outside the patient. In one or more embodiments, ablation electrode lines and implantable stimulators may adapt to specific requirements of various fields of application, such as stimulation and dissipation of signals to nerves, the brain, and other organs, or for the feed of implantable sensors.

FIG. 2 shows an actively fixable electrode line 20 with a proximal end 80 and a distal end 81, according to at least one embodiment of the invention. FIG. 2 shows an overview of a construction of electrode line 20 depicted as cut in the middle, wherein the entire length is not illustrated.

In one or more embodiments, electrode line 20, at its proximal end 80, includes a plug side, at which the electrode line 20 may be connected to the device 10. In at least one embodiment, at its distal end 81, the electrode line 20 may include a head side with an electrode head 50 to contact the tissue. In at least one embodiment, the electrode line 20 may include a bipolar electrode line and may include a coaxial construction.

At the proximal end 80, by way of at least one embodiment, the electrode line 20 may include a two-pole electrode line plug 34 with two coaxial plug contacts 36 and two rubber lip seals 38.

According to one or more embodiments, the electrode line 20 may include one or more of a coaxial twin-core line portion 40 with a helically coiled inner conductor 42, an insulation 46 located between the inner conductor and a helically wound outer conductor 44, and an insulating outer sleeve 48 that extends between the proximal end 80 and the distal end 81. In at least one embodiment, the inner conductor 42 and the outer conductor 44 each may connect one of the plug contacts 36 to an electrode pole at the distal end 32 of the electrode line 20. The central line portion 40, in one or more embodiments, may include a feed line between the electrode line plug 34 and the electrode head 50.

By way of at least one embodiment, the distal end 32 may include two electrode poles, such as a first electrode pole as a ring electrode 24' and a second electrode pole as a tip electrode 22', wherein tip electrode 22' includes a corkscrew-like helix to allow the electrode line 20 to be screwed actively into the heart tissue by screwing in the tip electrode 22', and may actively fix the distal end 81 of the electrode line 20. In at least one embodiment, the outer conductor 44 may contact the ring electrode 24', and the inner conductor 42 may contact the corkscrew-like actively fixable tip electrode 22'. One or more embodiments of the invention may include a metal head housing 52, in which the helical tip electrode 22' may be guided through, and which is arranged distally of the ring electrode 24'. The head housing 52, in at least one embodiment, may be electrically insulated on its outer face. In one or more embodiments, the head housing 52 may be electrically connected to the inner conductor 42 via a contact spring 54.

As shown in FIG. 2, at least one embodiment of the invention may include a contact point 56 that may electrically contact a second electrical component. The contact point 56, in at least one embodiment, may be located on the head housing 52. In one or more embodiments, the inner conductor 42 may include the first electrical component. The contact point 56 that electrically contacts the second electrical component at the electrode head, in at least one embodiment, may be located on the metal head housing 52 and approximately at the height of the tissue contact.

As shown in FIG. 2, at least one embodiment of the invention includes an actively fixable distal electrode line end 81 with a metal head housing 52 electrically connected to the corkscrew-like actively fixable tip electrode 22'. In one or more embodiments, the head housing 52 may be coated with a dielectric, of which the $\varepsilon_R$ may include an order of magnitude of 10000. In at least one embodiment, the dielectric slows a wave flowing in the head housing 52 and may include a frequency of 64 MHz, such that the period of oscillation over the path from the contact point 54 to the edge of the head housing 52 corresponds to a phase of $\pi/4$. In one or more embodiments, the dielectric may include ferroelectrics, such as barium titanate.

Figure 3:
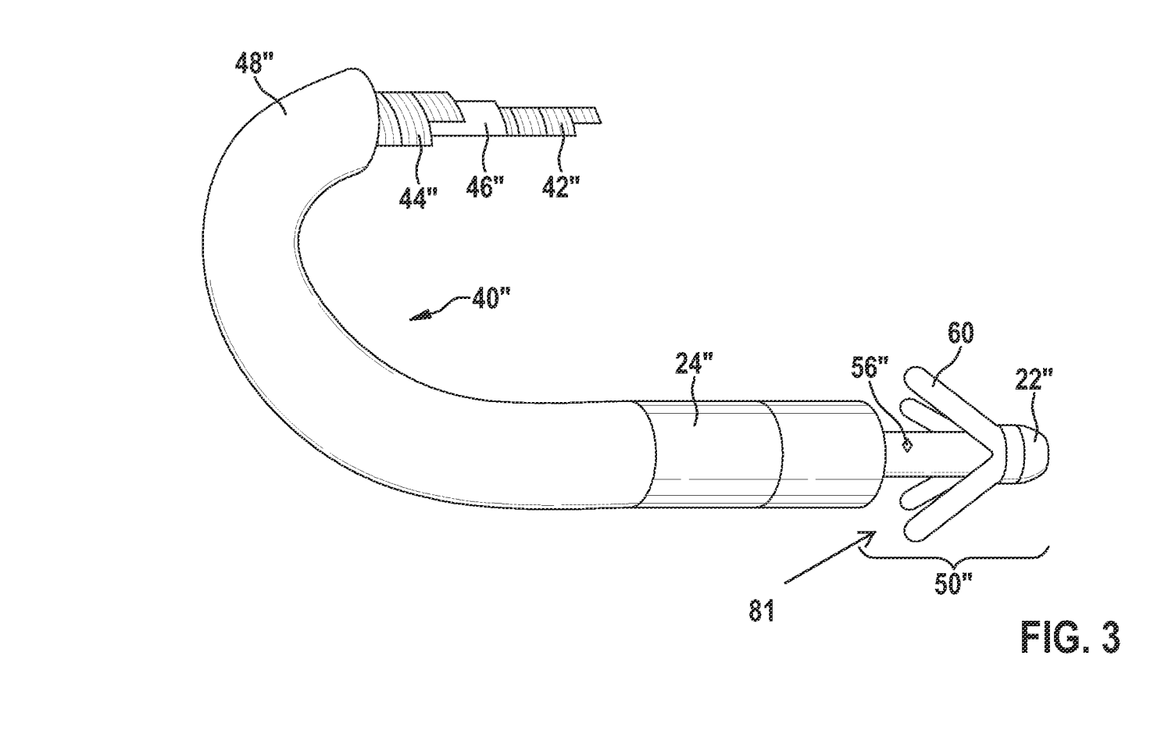
FIG. 3: shows a distal portion of a passively fixable electrode line, according to at least one embodiment of the invention.

FIG. 3 shows a distal longitudinal portion of an alternative electrode line according to at least one embodiment of the invention. As shown in FIG. 3, in one or more embodiments, the electrode line may include a line portion 40" with an inner conductor 42", an insulation 46" located between the inner conductor 42" and an outer conductor 44", and an outer insulating sleeve 48". At least one embodiment of the invention includes one or more of a proximal electrode pole, such as a ring electrode 24", and a tip electrode 22", such as a semi-spherical conductive surface at the distal tip of the electrode line. One or more embodiments may include four tines 60 located slightly proximally to the tip electrode 22". In at least one embodiment, the tines 60 may include soft plastic and may passively fix the distal end 81 of the electrode line 22". At least one embodiment of the invention may include a contact point 56" to connect to a second electrical component.

As shown in FIG. 3, one or more embodiments may include the distal region of an electrode line 20, with soft anchors or tines 60 in order to passively fix the electrode line in the tissue. In at least one embodiment, a region after the anchors 60 may include metal and therefore may be at the same time potential as the inner conductor 42" (such as the first electrical component). At least one embodiment of the invention may include an expedient contact point 56" to contact the second electrical component.

In one or more embodiments, the at least one second electrical component may include a conductor, such as a wire. In at least one embodiment, the wire may be wound around the respective electrode head 50 or 50" shown in at least FIGS. 2 and 4 for example. In one or more embodiments, the wire, electrically connected at one end to the electrode head 50 or 50", may be embedded on the electrode head 50 or 50" in a head insulation 58 or 58". The head insulation 58 or 58", in at least one embodiment, may include a material with high relative permittivity (>>10), such as a ferroelectric, or barium titanate. In at least one embodiment, a wave velocity in the wire 62' or 62" may be lowered, and the wavelength may be shortened. As such, one or more embodiments, with the reduced wire length (<100 cm), may remain in a range that cannot be reduced macroscopically.

Figure 4:
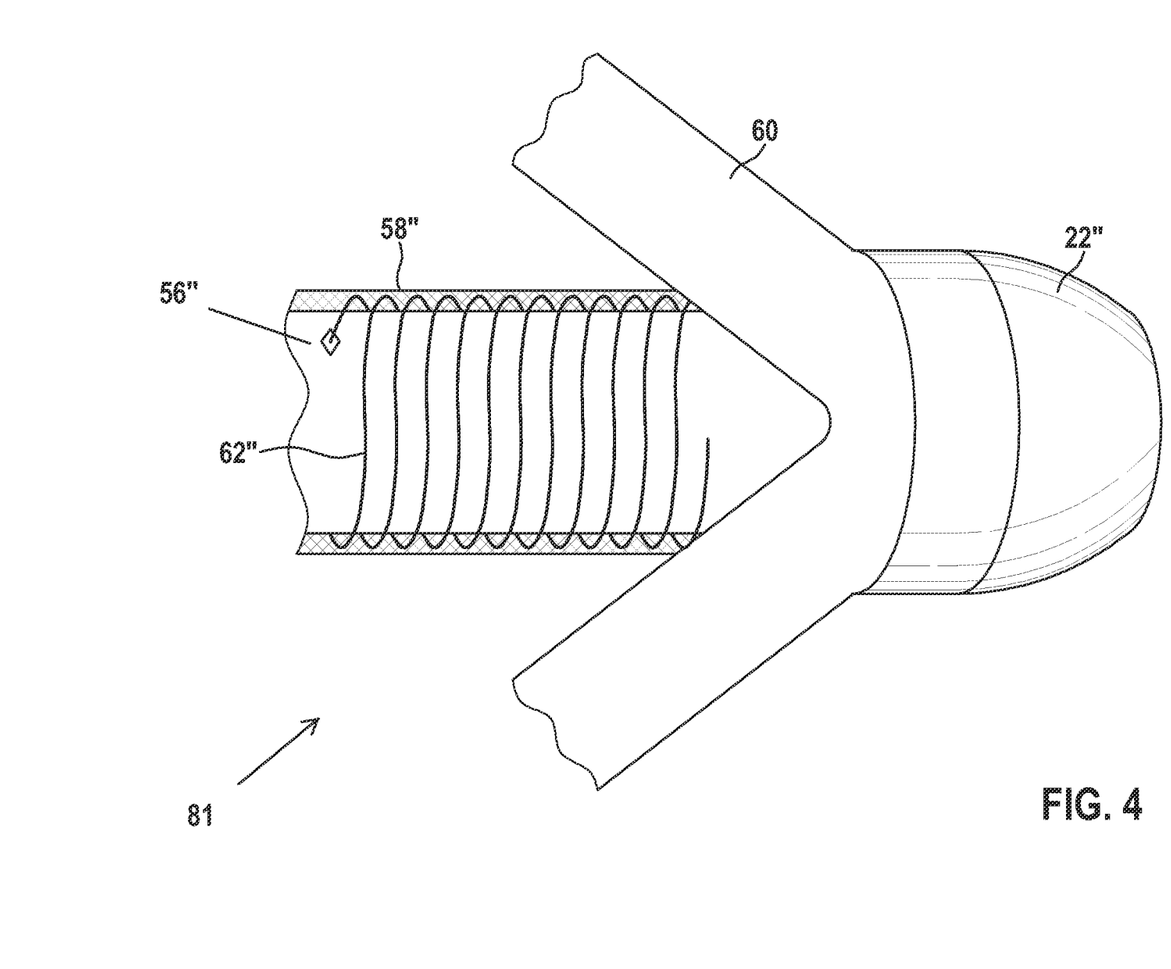
FIG. 4: shows a detail of the distal end of the electrode line of FIG. 3 with an electrical conductor wound around an electrode head as a second electrical component, according to at least one embodiment of the invention.

FIG. 4 shows a detail of the distal end 81 of the electrode line of FIG. 3, with an electrical conductor wound around an electrode head as a second electrical component, according to at least one embodiment of the invention. In at least one embodiment, the distal end 81 may include a second electrical component connected to the contact point 56", such as a helically coiled, insulated wire 62". FIG. 4 shows a passively fixable electrode head, according to at least one embodiment, that may include a second electrical component connected to the first electrical component (such as the inner conductor 42"). In one or more embodiments, the second electrical component may include the insulated metal wire 62", which may be connected at the contact point 56" to a shaft of the electrode head. In at least one embodiment, the wire 62" may be insulated with respect to the shaft outside the contact point 54".

According to one or more embodiments, due to the helically coiled form of the insulated wire 62" as an electrical conductor of the second electrical component and due to the relative permittivity $\varepsilon_R$ of the head insulation surrounding the wire, the second electrical component may include small outer dimensions and may include an electrical length that corresponds at least to a tenth of the wavelength of electromagnetic waves in the radio frequency range that the first conductor is subjected to. In at least one embodiment, the wavelength of electromagnetic alternating fields in the radio frequency range may be between 10 MHz and 400 MHz and may be between 30 m (at 10 MHz) and 75 cm (at 400 MHz) in vacuum. Due to the inductances of the electrical conductor 64" caused by the helix shape and due to a capacitance per unit length caused by the relative permittivity of the insulating material surrounding the electrical conductor 64", by way of one or more embodiments, the electrical conductor 64" of the second electrical component may be shorter in terms of its geometric length than the extent to which it corresponds to the corresponding fraction of the wavelength in vacuum, since the wavelength at a given frequency on the electrical conductor may be shorter than in a vacuum.

FIG. 5 shows a detail of the distal end of an actively fixable electrode line of FIG. 2 with an electrical conductor wound around a central functional conductor as a second electrical component, according to at least one embodiment of the invention. As shown in FIG. 5, one or more embodiments of the invention include an actively fixable electrode head including a screw head that may include a second electrical component, wherein the second electrical component may be electrically connected to the inner conductor 42' as a first electrical component. In at least one embodiment, the second electrical component may include an insulated metal wire 62', and may be connected at the contact point 56' to the shaft of the electrode head 50. In one or more embodiments of the invention, the insulated wire may be wound externally onto the head housing 52'.

Figure 6:
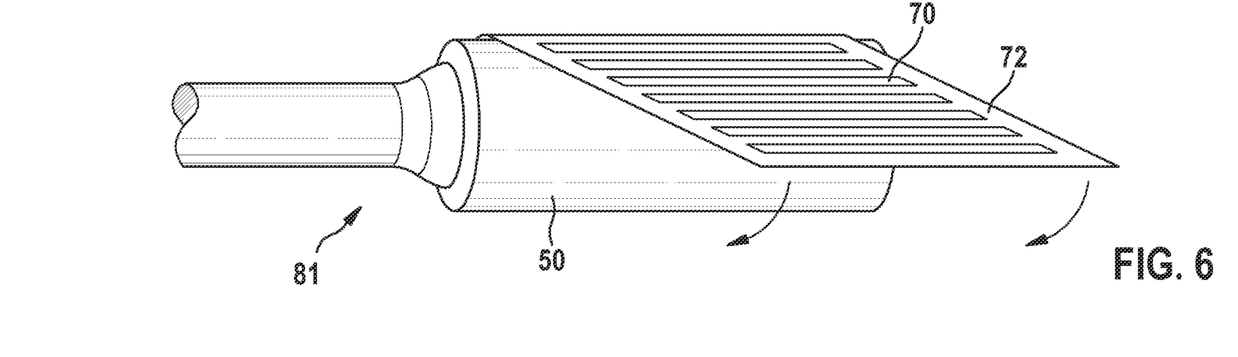
FIGS. 6 and 7: show a detail of the distal end of an actively fixable electrode line of FIG. 2 with an electrical conductor wound around a head housing on a flexible conductive track as a second electrical component, according to at least one embodiment of the invention.

FIGS. 6 and 7 show the distal end 32 of an actively fixable electrode line 20 of FIG. 2, according to at least one embodiment of the invention. As shown in FIGS. 6 and 7, in one or more embodiments, the second electrical component may be wound around the metal electrode head 50, such as around the metal head housing 52. In at least one embodiment, the second electrical component may include a coiled conductive track 70 on a flexible support material 72, such as a flexible sheet. The conductive track 70, in one or more embodiments, may electrically connect to the contact point 56 (shown in FIG. 2) and may electrically connect, via the contact point 56, to the inner conductor 42 and the electrode line 20. FIG. 6 shows a flexible support material 72 that may be wound with the conductive track 72 around the electrode head 50, as shown in FIG. 7, according to at least one embodiment of the invention. In one or more embodiments, the second electrical component wound around the electrode head 50 may be embedded in a dielectric having a high relative permittivity $\varepsilon_R$.

Figure 8:
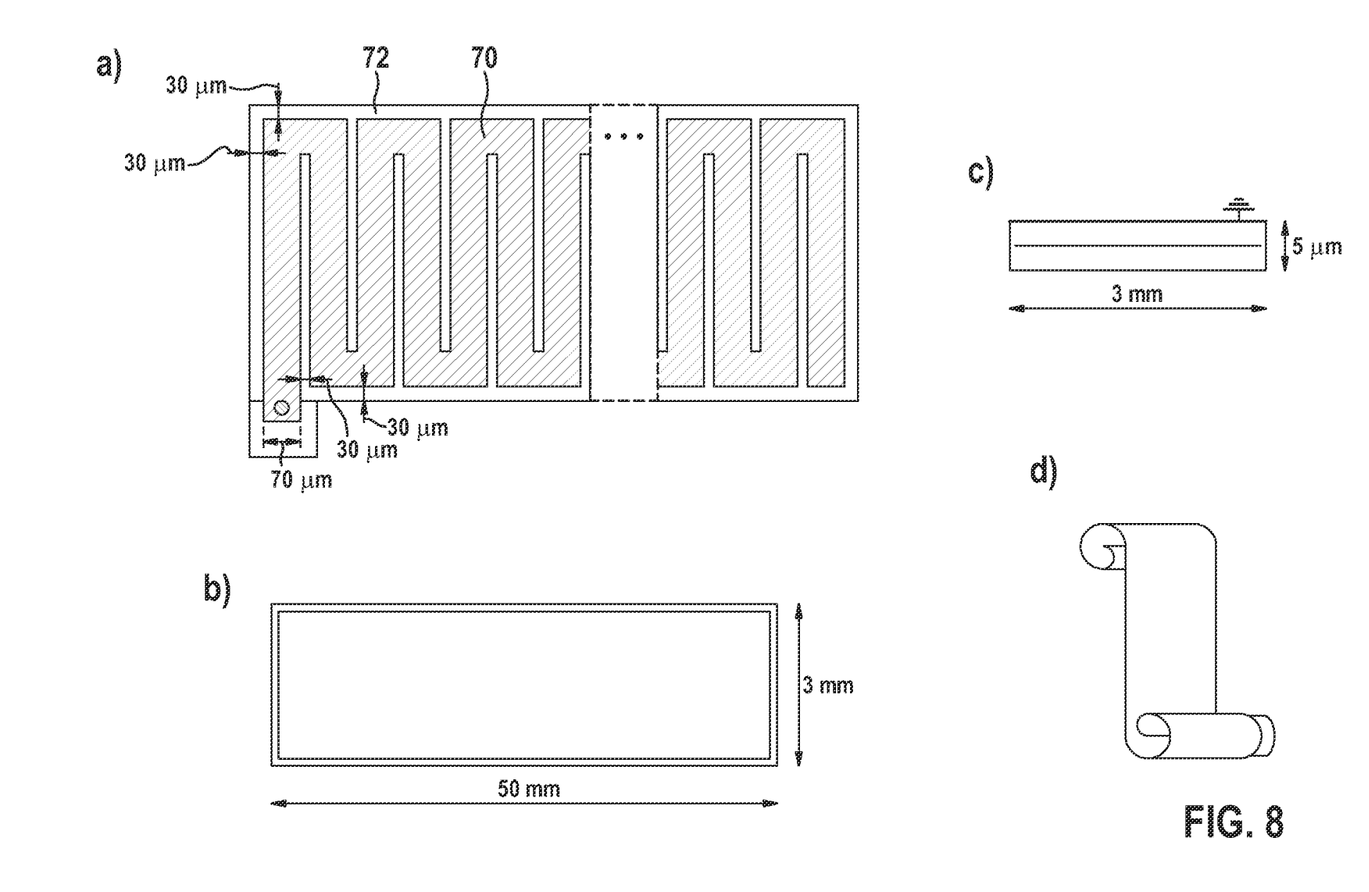
FIGS. 8 and 9: show variants of electrical conductors applied to a sheet, the electrical conductors together with the sheet as a flexible printed circuit board forming a second electrical component, according to at least one embodiment of the invention.
Figure 9:
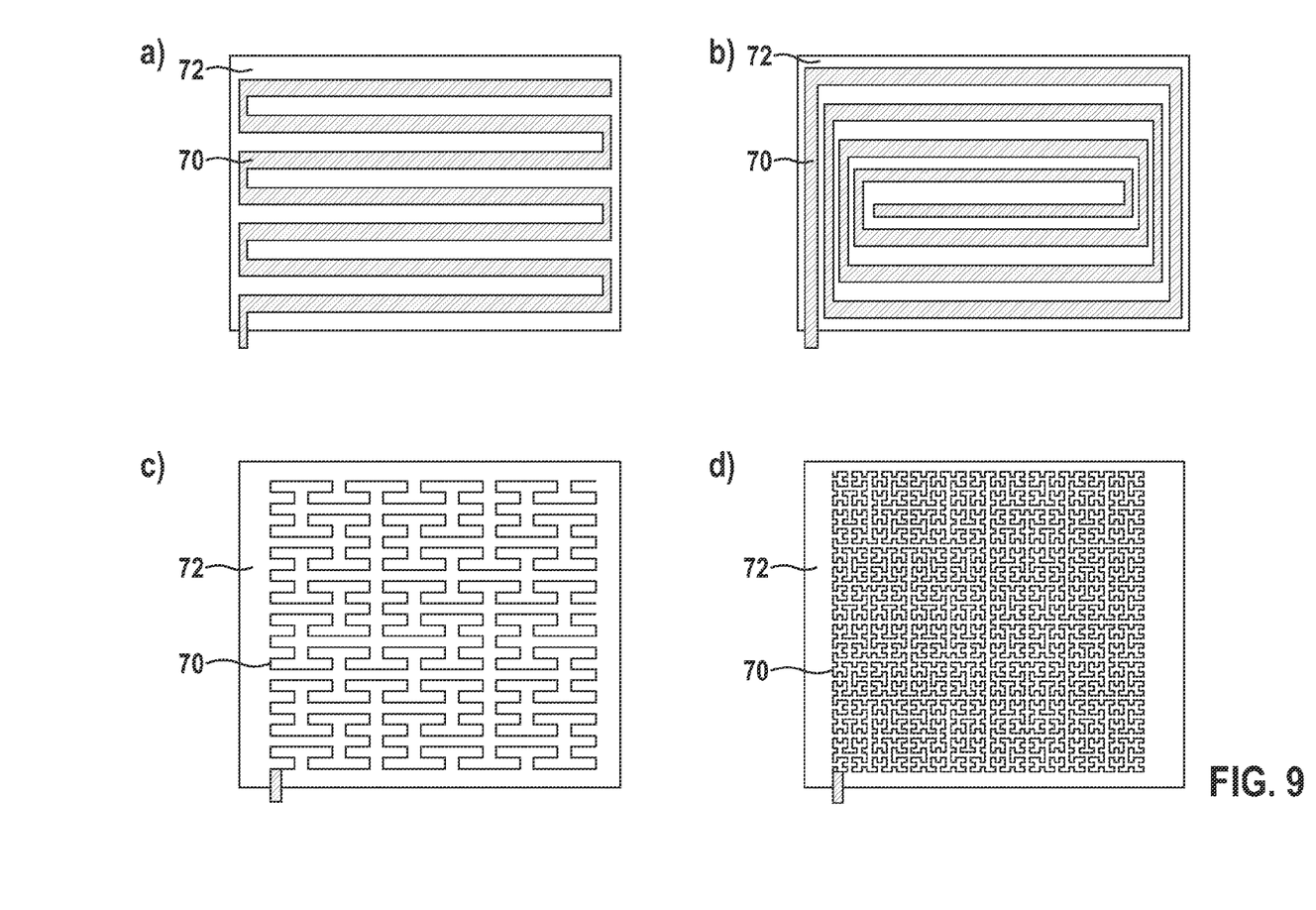

FIGS. 8 and 9 show variants of electrical conductors applied to a sheet, the electrical conductors together with the sheet as a flexible printed circuit board forming a second electrical component, according to at least one embodiment of the invention. As shown in FIG. 8, one or more embodiments include the flexible support material 72 and the conductive track 70 located thereon, showing example dimensions of the components. In at least one embodiment, the flexible support material 72 with the conductive track 70 may be between 3 and 8 μm thick and may include a length, as a length in the longitudinal direction of the electrode line, between 2 and 5 mm. In one or more embodiments, the unwound width, such as 50 mm, depends on the electrical length of the conductive track 70. In at least one embodiment, as shown in FIG. 8, the conductive track 70 may include a width of 70 μm. One or more embodiments may include widths between 50 and 100 μm. As also shown in FIG. 8, in at least one embodiment, the conductive track 70 may include a zigzag shape and may run in a zigzag-shaped manner over the flexible support 72.

As shown in FIG. 9, one or more embodiments may include various courses of the respective conductive track 70 over the flexible support material 72 represented by illustrations 9 a) to 9 d). According to at least one embodiment, illustration 9 a) shows a zigzagged course, illustration 9 b) shows a spiraled course and illustrations 9 c) and 9 d) show meandering courses of the conductive track 70.

Figure 10:
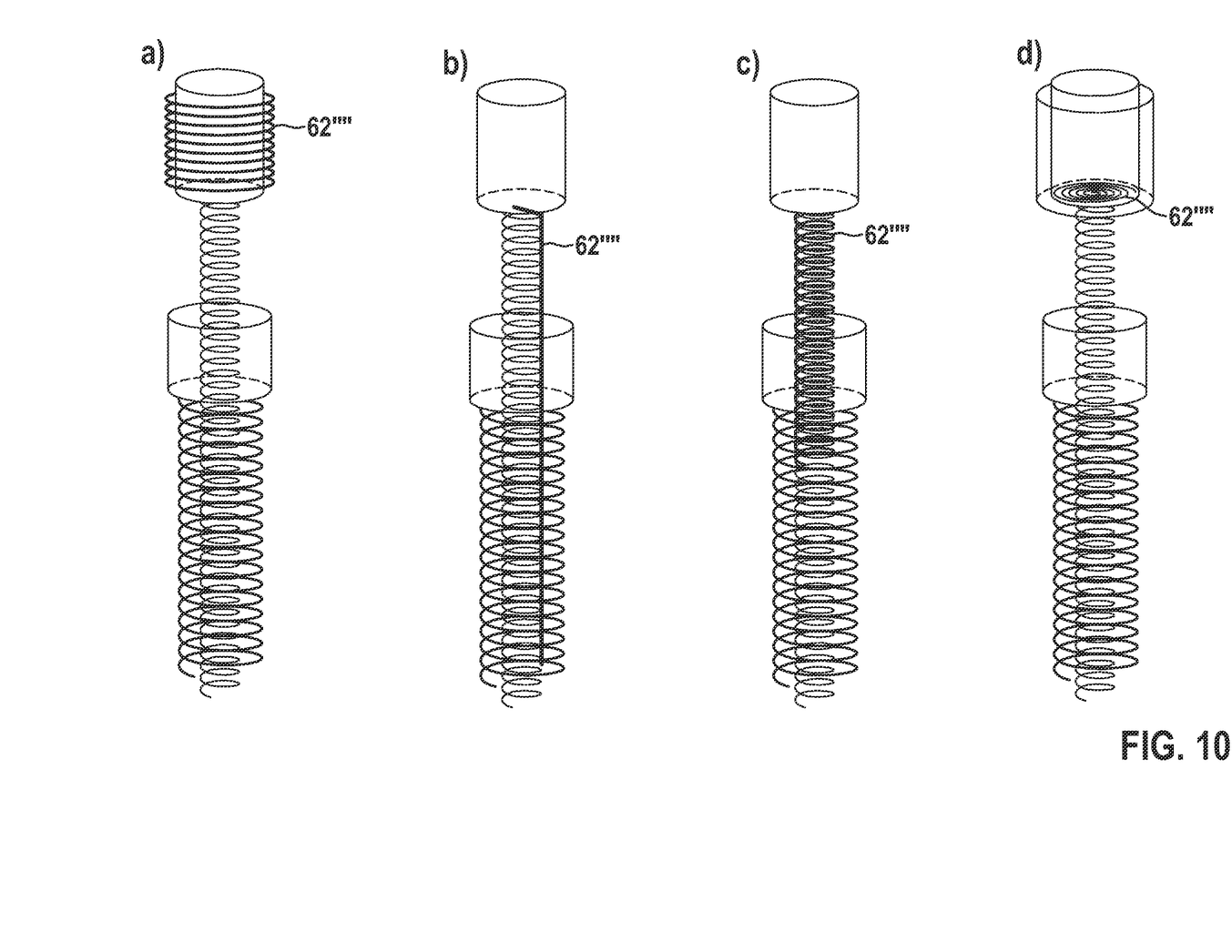
FIG. 10: shows an implantable heart stimulator and an implantable electrode line connected thereto, according to at least one embodiment of the invention.

FIG. 10 shows an implantable heart stimulator and an implantable electrode line connected thereto, according to at least one embodiment of the invention. As shown in FIG. 10, one or more embodiments may include various structures of how the conductor 62"" of the second electrical component may be laid in a coaxial electrode line, represented by illustrations 10 a) to 10 d). According to at least one embodiment, as shown in illustration 10 a), the conductor 62"" may be wound helically around a distal electrode pole.

According to one or more embodiments, as shown in illustration 10 b), the conductor 62'''', starting from the distal electrode pole, may run in an elongate manner in the proximal direction of the electrode line. According to at least one embodiment, as shown in illustration 10 c), the conductor 62'''' of the second electrical component may include a helix, and may run coradially in the proximal direction with the helix of the inner conductor, starting from the distal electrode pole.

According to one or more embodiments, as shown in illustration 10 d), the conductor 62'''' of the second electrical component may be arranged and run in a spiraled manner at the proximal end of the distal electrode pole.

By way of one or more embodiments, other variants may include a coradial and a multi-lumen structure of the electrode line. At least one embodiment of the invention may include a multi-lumen structure, wherein the individual conductors are not coiled or are only coiled in part. In one or more embodiments, the conductor of the second electrical component of a multi-lumen structure may be guided in a manner as discussed above regarding illustrations 10 a) to 10 d).

In one or more embodiments, the wire, such as the conductor of the second electrical component, may be arranged in a meandering, braided or randomly "intertwined" manner.

In at least one embodiment, a stranded wire or a cable, electrically conductively connected to the end of the electrode head, may be embedded as a conductor of the second electrical component in the head insulation. In one or more embodiments, the stranded wire or the cable may include a separate insulation.

In one or more embodiments, the wire may be matched to the wavelength of the coupled-in high-frequency energy protrudes, as a conductor of the second electrical component, beyond the electrode head in the proximal direction of the electrode line, and may be embedded in the insulation of the adjoining electrode body.

By way of at least one embodiment, the electrode head may include a connection point between a surface electrode, for example a defibrillation electrode for the heart, and the electrode conductor supplying the energy (such as the functional conductor). As such, in one or more embodiments, an insulated wire as a conductor of the second electrical component, with or without the separate insulation, may be connected to the electrode head, and may be matched, parallel to the surface electrode, to the wavelength of the coupled-in high-frequency energy.

In at least one embodiment, the second electrical component may include a very thin wire (such as a wire of 50 μm), which may be wound coaxially with the feed line (such as the first electrical component) around the electrode head, wherein the winding may include a very small pitch of <100 μm.

In one or more embodiments, the electrical conductor may include one or more of a straight, wound, double-spiraled, spiraled, spirally wound, fractal, meandering, and intertwined geometries.

According to at least one embodiment of the invention, methods of producing the line geometry may include one or more of laser cutting, casting, winding, printing (for example screen printing or pad printing), machining (milling, turning, grinding . . . ), etching, PVD, CVD, sputtering, stamping, and galvanic deposition.

In at least one embodiment, methods of producing the dielectrically effective body or the combination with the line geometry may include one or more of dip coating and sintering.

According to one or embodiments, dip coating and sintering of the dielectric body may include a sintered compact body, or may be sintered in combination with the electrical conductor by one or more of injection molding, melting, extrusion, and electrostatic deposition (such as powder coating).

In at least one embodiment, the natural number n may include a range of n=0 to n=2. With an open (insulated) end, in one or more embodiments, the reflection may lead to a node of a stationary wave at the point of tissue contact.

One or more embodiments of the invention may include a feed line that may include a central line portion of an electrode line, wherein the feed line may include the first electrical component and a second electrical component in the region of anticipated anti-nodal points. In at least one embodiment, the feed line may be cut to any length to accommodate different variants and subsequently trimmed therefrom.

In at least one embodiment, the second electrical component may include a plurality of continuing conductors of different electrical length, such as two or more conductors, such that the second electrical component may be effective at a number of coupled-in frequencies.

In one or more embodiments, the conductor or the plurality of conductors of the second electrical component may include a different conductor width along the length in order to be effective in a wide-band manner. In at least one embodiment, the conductor or the plurality of conductors may be linear and may be formed in a linear manner (starting from the contact point), or may be tapered, formed by tapering, in stages.

One or more embodiments of the invention may include electrophysiology catheters, wherein the conductor of the second electrical component may be combined with visualization coils in order to improve visibility of the distal end of the catheter in an MR image.

By way of at least one embodiment, the combination of continuing electrical conductors of the second electrical component and the support material thereof may be electrically connected to the inner conductor in the distal region of an electrode line, and may be one or more of:
    attached externally on the head housing,
    attached internally in the head housing,
    attached within the head housing on a shaft for a corkscrew-like tip electrode,
    assembled below a ring electrode,
    or may form a portion of the head housing.

According to at least one embodiment, the support materials for the conductor of the second electrical component, such as the sheet 72, and the dielectric may include one or more of varnish, ceramic, glass, and polytetrafluoroethylene, or the like.

In one or more embodiments, the electrical conductor of the second electrical component may be guided from the point of contact (contact point) of the therapeutic and/or diagnostic functional conductor in the distal direction, and may be guided in a wound or meandering manner.

One or more embodiments of the invention may include a miniaturized device, due to the use of dielectrically effective embedding of the second electrical component. In at least one embodiment, due to the parallel connection, the second electrical component may have little to no influence on functional properties of the implantable device. One or more embodiments include mechanically and electrically robust components. In at least one embodiment, the second electrical component may be effective for different frequencies of an electromagnetic wave. By way of one or more embodiments, the demands on dimensional tolerance may be low.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable medical device comprising:
   at least one elongate electrical line, wherein the at least one elongate electrical line comprises
      a first electrical component, wherein the first electrical component or a portion of the first electrical component comprises a functional conductor;
      an electrode head disposed at a distal end of the first electrical component, wherein the electrode head comprises a contact point; and,
      at least one second electrical component in electrical contact with the first electrical component, wherein the at least one second electrical component comprises
         an electrical conductor comprising a first end, a second end and an electrical conductor length that is insulated completely along or along part of the electrical conductor length,
         wherein the first end is electrically connected to the contact point of the electrode head and wherein the second end is configured to electrically connect to a tissue capacitively, inductively or galvanically,
         wherein the electrical conductor length corresponds to at least a tenth of a wavelength of electromagnetic waves in a radiofrequency range that said first electrical component is subjected to,
         wherein the electrical conductor further comprises one of a meandered coil shape, a helically wound shape and a spirally wound shape,
         wherein the outer dimension of the electrical conductor is smaller than the electrical conductor length; and,
      a flexible support material that is wound around the first electrical component and a conductive track disposed on said flexible support material.

2. The implantable medical device as claimed in claim 1, wherein the at least one elongate electrical line further comprises at least one electrode pole, and wherein the functional conductor is connected to the at least one electrode pole that is configured to deliver therapy signals and/or detect diagnosis signals.

3. The implantable medical device as claimed in claim 2, further comprising an electrode line, wherein the at least one elongate electrical line is disposed at a distal end of the electrode line, and wherein the electrode line is configured to connect to a therapy device, a monitoring device or a therapy and monitoring device.

4. The implantable medical device as claimed in claim 3, wherein the electrode line further comprises a proximal end configured to connect to the therapy device, the monitoring device or the therapy and monitoring device, and the distal end of the electrode line is remote from the proximal end of the electrode line, wherein the distal end comprises the at least one electrode pole and the at least one second electrical component.

5. The implantable medical device as claimed in claim 3, wherein the electrode line further comprises a longitudinal portion, such that the at least one second electrical component is wound around the longitudinal portion.

6. The implantable medical device as claimed in claim 4, wherein the electrode line further comprises a longitudinal portion, such that the at least one second electrical component is wound around the longitudinal portion.

7. The implantable medical device as claimed in claim 1, wherein the at least one second electrical component further comprises a dielectrically effective medium, wherein the electrical conductor thereof is surrounded completely or in part by the dielectrically effective medium, and wherein the dielectrically effective medium comprises a relative permittivity $e_R$ greater than 10.

8. The implantable medical device as claimed in claim 7, wherein the dielectrically effective medium or portions of the dielectrically effective medium further comprises a material of one or more of a ferroelectric and at least one of glass, barium titinate, polyethylene, silicon oxide, silicon carbide, ceramic, piezo materials, aluminum oxide, titanium oxide, tantalum oxide, semiconductor materials, and plastics.

9. The implantable medical device as claimed in claim 1, wherein the at least one second electrical component further comprises at least one line end, and is configured to contact the tissue at a distance $n*\frac{1}{2}$ of a wavelength in the radiofrequency range from the at least one line end, and wherein n is a natural number in a range of n=1 to n=2.

10. The implantable medical device as claimed in claim 7, wherein the first electrical component further comprises an electrically conductive surface, and wherein the at least one second electrical component and the dielectrically effective medium are in contact with the electrically conductive surface.

11. The implantable medical device as claimed in claim 8, wherein the first electrical component further comprises an electrically conductive surface, and wherein the at least one second electrical component and the dielectrically effective medium are in contact with the electrically conductive surface.

12. The implantable medical device as claimed in claim 1, wherein the electrical conductor length of the at least one second electrical component comprises a length matched to a frequency range between 10 MHz and 400 MHz or between 40 MHz and 150 MHz.

13. The implantable medical device as claimed in claim 1, wherein the quarter of the wavelength of electromagnetic waves in the radiofrequency range is from 40 MHz to 150 MHz.

14. An implantable medical device comprising:
   at least one elongate electrical line, wherein the at least one elongate electrical line comprises
      a first electrical component, wherein the first electrical component or a portion of the first electrical component comprises a functional conductor;
      an electrode head disposed at a distal end of the first electrical component, wherein the electrode head comprises a contact point; and,
      a second electrical component wound around the electrode head and in electrical contact with the first electrical component and the functional conductor, wherein the second electrical component comprises a flexible support material comprising a flexible sheet; and,
a conductive track on said flexible support material, wherein the conductive track is a coiled conductive track comprising an electrical conductor having a first end, a second end and an electrical conductor length that is insulated completely along or along part of the electrical conductor length,
wherein the electrical conductor length corresponds to at least a tenth of a wavelength of electromagnetic waves in a radiofrequency range that said first electrical component is subjected to.

15. An implantable medical device comprising:
at least one elongate electrical line, wherein the at least one elongate electrical line comprises
a first electrical component, wherein the first electrical component or a portion of the first electrical component comprises a functional conductor;
an electrode head disposed at a distal end of the first electrical component, wherein the electrode head comprises a contact point; and, at least one second electrical component in electrical contact with the first electrical component, wherein the at least one second electrical component comprises
an electrical conductor having a first end, a second end and an electrical conductor length that is insulated completely along or along part of the electrical conductor length,
wherein the first end is electrically connected to the contact point of the electrode head and wherein the second end is configured to electrically connect to a tissue capacitively, inductively or galvanically,
wherein the electrical conductor length corresponds to at least a tenth of a wavelength of electromagnetic waves in a radiofrequency range that said first electrical component is subjected to, and
a flexible support material and a conductive track on said flexible support material,
wherein the flexible support material, the conductive track and the electrical conductor are wound around the electrode head, and are embedded in a dielectric having a high relative permittivity $e_R$.

16. An implantable medical device comprising:
at least one elongate electrical line, wherein the at least one elongate electrical line comprises
a first electrical component, wherein the first electrical component or a portion of the first electrical component comprises a functional conductor;
an electrode head disposed at a distal end of the first electrical component, wherein the electrode head comprises a contact point; and,
a second electrical component, wherein the second electrical component is a flexible printed circuit board wound around the first electrical component, and wherein the flexible printed circuit board comprises
a flexible sheet; and
a conductive track on said flexible support material, wherein the conductive track comprises an electrical conductor having a first end, a second end and an electrical conductor length that is insulated completely along or along part of the electrical conductor length,
wherein the first end is electrically connected to the contact point of the electrode head and the second end is configured to electrically connect to a tissue capacitively, inductively or galvanically, and,
wherein the electrical conductor length corresponds to at least a tenth of a wavelength of electromagnetic waves in a radiofrequency range that said first electrical component is subjected to.

* * * * *